United States Patent
Kaufman et al.

(10) Patent No.: US 7,225,005 B2
(45) Date of Patent: May 29, 2007

(54) OPTICAL DETERMINATION OF IN VIVO PROPERTIES

(75) Inventors: Howard B. Kaufman, Newtown, MA (US); Alex R. Zelenchuk, Stoughton, MA (US)

(73) Assignee: Intelligent Medical Devices, Inc., Cambridge, MA (US)

( * ) Notice: Subject to any disclaimer, the term of this patent is extended or adjusted under 35 U.S.C. 154(b) by 42 days.

(21) Appl. No.: 11/011,714

(22) Filed: Dec. 14, 2004

(65) Prior Publication Data

US 2006/0129037 A1   Jun. 15, 2006

(51) Int. Cl.
*A61B 5/00* (2006.01)
(52) U.S. Cl. ...................... 600/322; 600/310
(58) Field of Classification Search .............. 600/309, 600/310, 322, 323
See application file for complete search history.

(56) References Cited

U.S. PATENT DOCUMENTS

| | | | |
|---|---|---|---|
| 4,998,533 A | | 3/1991 | Winkelman |
| 5,598,842 A | * | 2/1997 | Ishihara et al. ............. 600/322 |
| 5,787,185 A | | 7/1998 | Clayden |
| 5,983,120 A | | 11/1999 | Groner et al. |
| 6,104,939 A | | 8/2000 | Groner et al. |
| 6,353,750 B1 | * | 3/2002 | Kimura et al. ............. 600/344 |
| 6,374,128 B1 | * | 4/2002 | Toida et al. ................ 600/310 |
| 6,411,839 B1 | * | 6/2002 | Okinishi ..................... 600/479 |
| 6,438,396 B1 | | 8/2002 | Cook et al. |
| 6,650,916 B2 | | 11/2003 | Cook et al. |
| 2002/0111546 A1 | * | 8/2002 | Cook et al. ................. 600/322 |
| 2004/0024296 A1 | | 2/2004 | Krotkov et al. |

OTHER PUBLICATIONS

Inoué, Shinya, "Foundations of Confocal Scanned Imaging in Light Microscopy", *Handbook of Biological Confocal Microscopy: Confocal Scanned Imaging and Light Microscopy*, Chapter 1, pp. 1-17.
Schmitt et al., "New Methods For Whole Blood Oximetry", *Anals of Biomedical Engineering*, vol. 14, pp. 35-52 (1986).

(Continued)

*Primary Examiner*—Eric Winakur
*Assistant Examiner*—Etsub Berhanu
(74) *Attorney, Agent, or Firm*—Sullivan & Worcester LLP

(57) ABSTRACT

A system and method for determining an in vivo property of a tissue or blood is described. The in vivo property may be a hematocrit value, a hemoglobin concentration, or a combination thereof. The system can automatically determine a location of a subcutaneous blood vessel. Based on the automatically determined location, the system illuminates the blood vessel with a light beam and detects light resulting from the illumination. The system determines the in vivo property based on the detected light. Alternatively, or in combination, the system displays an image corresponding to a spatial relationship between a subcutaneous blood vessel and a light beam. Based on the image, an operator can adjust the light beam with respect to the blood vessel to have a selected spatial relationship. The system determines an in vivo property based on the illumination of the blood vessel when the light beam has the selected spatial relationship.

27 Claims, 10 Drawing Sheets

OTHER PUBLICATIONS

Steinke et al., "Reflectance measurements of hematocrit and oxyhemoglobin saturation", *American Physiological Society*, pp. H147-H153.

Webb, Robert H., "[1] Theoretical Basis of Confocal Microscopy", *Methods In Enzymology*, vol. 307, pp. 3-20.

Bohren, C.F. et al., Absorption and Scattering of Light by Small Particles, New York, Wiley & Sons, 1983, 477-482 pgs.

Reynolds, L.O. et al. Diffuse Reflectance From A Finite Blood Medium: Applications To The Modeling Of Fiber Optic Catheters, Applied Optics, 15(9), 1976, pp. 2059-2067.

Theoretical models and parameters useful for such models are discussed in, e.g., Reynolds, L.O., Optical Diffuse Reflectance and Transmittance From An Anisotropically Scattering Finit Blood Medium, Ph.D. Thesis, Dept. Electrical Eng., Univ. of Wash., 1975.

* cited by examiner

OPTICAL DETERMINATION OF IN VIVO PROPERTIES

FIELD OF THE INVENTION

The invention relates to the optical determination of in vivo properties of a tissue or blood.

BACKGROUND

Medical personnel often need to determine properties of human or animal tissue or blood. For example, in a diagnostic or surgical setting, one may wish to determine blood hematocrit (Hct), which relates to the abundance of hemoglobin (Hb) and/or red blood cells. Traditional determinations of Hct include drawing blood from a vein and centrifuging the drawn blood to separate cellular and fluid components of the blood.

SUMMARY OF THE INVENTION

One aspect of the present invention relates to the optical determination of an in vivo property of a tissue or blood and related methods and systems. In various embodiments, the in vivo property is an Hct value, an Hb concentration, or combination thereof. Unless otherwise specified, the in vivo property may be a relative value or an absolute value.

In general, the invention features systems that automatically determine a location of a subcutaneous blood vessel. The systems illuminate the automatically located blood vessel with a light beam and detect light resulting from the illumination. The systems determine an in vivo property based on the detected light.

In some embodiments, the systems display an image corresponding to a spatial relationship between a subcutaneous blood vessel and a light beam. Based on the image, an operator can adjust the light beam with respect to the blood vessel and/or move the blood vessel with respect to the light beam so that the light beam and blood vessel have a selected spatial relationship, e.g., the light beam may intersect the blood vessel. The systems determine an in vivo property based on the illumination of the blood vessel with a light beam having the selected spatial relationship.

In some embodiments, the systems obtain optical data indicative of a spatial relationship between a subcutaneous blood vessel and a light beam. The systems signal an operator, e.g., by audio or visual signal, if the blood vessel and light beam do not have a selected spatial relationship. If necessary, the operator can adjust the spatial relationship between the light beam and blood vessel. The systems can signal the operator when the selected spatial relationship has been achieved. The systems determine an in vivo property based on the illumination of the blood vessel with a light beam having the selected spatial relationship.

In some embodiments, the system includes an optical device configured to project a light beam onto a tissue of a subject, an imaging device configured to generate optical data, and a device to display an image corresponding to the optical data. The image indicates a spatial relationship between the light beam and a blood vessel within the tissue. A user can manipulate the optical device and, based on the image, bring the light beam and the blood vessel into a selected spatial relationship. The system also includes a detector configured to generate a detector signal corresponding to light resulting from illumination of the blood vessel with the light beam having the selected spatial relationship. A processor determines an in vivo blood property based on the detector signal.

The imaging device can be configured to illuminate the tissue with light having a wavelength between about 400 and 1250 nm. The light may cover a spatial extent that is substantially greater than a diameter of the blood vessel.

A first portion of the detector signal may correspond to light that has passed a first distance within the blood vessel and a second portion of the detector signal may correspond to light that has passed a second, different distance within the blood vessel. The processor determines the in vivo blood property based on the first and second portions of the detector signals.

The projected light beam, when in the selected spatial relationship with the blood vessel, may have a width within the blood vessel that is about the same as or smaller than a difference between the first and second distances.

The in vivo property may be a hematocrit value, an abundance of hemoglobin, or a combination thereof.

In some embodiments, the system includes a device configured to automatically determine a location of a subcutaneous blood vessel, a light source configured to illuminate a located blood vessel with light, a detector to detect light resulting from the illumination and generate a detector signal from the detected light, and a processor configured to receive the detector signal and determine an in vivo blood property based on the detected light.

The light source can include a plurality of light guides each configurable to project a light beam onto a respective different portion of a subject's skin.

The detector can be configured to detect light that has passed first and second different distances within an illuminated located blood vessel. The processor determines the in vivo property based on the light that has passed the first and second different distances. The detector can be a multidimensional detector having a plurality of detector elements and at least first and second detector light guides. The first and second detector light guides respectively transmit the light that has passed the first and second different distances to different detector elements.

Another aspect of the invention relates to a method for determining an in vivo blood property. The method includes, displaying an image including at least one subcutaneous blood vessel. The image indicates a spatial relationship between a light beam derived from a light source and the blood vessel. Based on the image, the spatial relationship between the light beam and the blood vessel is modified so that the light beam illuminates the blood vessel. Light resulting from the illumination of the blood vessel by the light beam is detected. An in vivo blood property is determined based on the detected light.

In some embodiments, changing the spatial relationship includes manually changing a position of the light beam with respect to the blood vessel.

Determining an in vivo blood property can include determining an Hematocrit, an abundance of hemoglobin, or combination thereof.

In some embodiments, a method includes automatically determining a location of a blood vessel of a subject, illuminating the blood vessel with a light beam, detecting light resulting from illuminating the blood vessel, and determining an in vivo blood property based on the detected light. The method can include illuminating skin of the subject with light, detecting light resulting from the illumination of the skin, and determining the location of the blood vessel based on the detected light resulting from the illumination of the skin. Detecting light resulting from the illumination of the skin can include transmitting light through a plurality of different optical fibers each coupled to at least one detector element of a multidimensional detector. Detecting light resulting from the illuminating can include detecting a first portion of light having exited the skin a first distance away from the light beam and a second portion of light having exited the skin a second, different distance away from the light beam. The in vivo property is determined based on the first and second portions of light.

Illuminating a blood vessel can include projecting a light beam from a light guide.

Illuminating a blood vessel can include scanning light over the skin.

The method can include displaying an image corresponding to a spatial relationship between the blood vessel and a light beam projected onto the skin of the subject, and wherein, based on the image, a user can manually bring the blood vessel and light beam into a selected spatial relationship.

In another embodiment, a method includes illuminating a portion of a subject with light from a light source, the illuminated portion of the subject including a blood vessel, detecting light from the illuminated portion of the subject, determining a location of a blood vessel based on light detected from the illuminated portion of the subject, illuminating the blood vessel with a light beam, detecting first light that has passed a first distance within the blood vessel from the light beam and second light that has passed a second, different distance within the blood vessel from the light beam, and determining an in vivo blood property based on the first and second light.

Illuminating the portion of the subject and illuminating the blood vessel with a light beam can be performed as part of the same step.

Detecting the light from the illuminated portion of the subject and the detecting the first and second light can be performed as part of the same step.

Illuminating a portion of a subject with light from a light source can include scanning the portion of the subject with a light beam.

Determining an in vivo blood property can include determining a hematocrit value, an abundance of hemoglobin, or a combination thereof.

Another aspect of the invention relates to a system for determining a blood property. The system includes a light source configured to illuminate a subject with light and comprising a plurality of optical fibers each configured to project a light beam onto a different portion of a subject, a detector, e.g., a multidimensional detector having a plurality of detector elements, that detects light arising from the illumination of the subject with light and from the projection of the light beams onto the different portions of the subject and that generates detector signals corresponding to the detected light, and a processor configured to: process detector signals to locate at least one subcutaneous blood vessel, operate the light source to illuminate the blood vessel with a light beam projected by at least one of the plurality of optical fibers, receive first and second detector signals corresponding to light that has passed first and second different distances within the blood vessel from the light beam, and determine a hematocrit, an abundance of hemoglobin, or a combination thereof based upon the first and second detector signals.

Another aspect of the invention relates to a system including a light source to illuminate a tissue of a subject with light, a detector, e.g., a multidimensional detector having a plurality of detector elements, a plurality of light guides each in optical communication with at least one different detector element and configured to transmit light resulting from illumination of the tissue to the at least one different detector element, and a processor to automatically determine a location of a blood vessel based on light detected by the multidimensional detector.

Another aspect of the invention relates to a system including a light source to illuminate skin of a subject with light, a detector, e.g., a multidimensional detector having a plurality of detector elements, to detect light resulting from illumination by the light source, a device to introduce a material beneath the skin of the subject, the device introducing the material via a target site, and a device to display an image comprising an image of at least one subcutaneous blood vessel and corresponding to a spatial relationship between the subcutaneous blood vessel and the target site.

The systems and methods can be used and/or implemented by, e.g., medical professionals such as in an emergency room or operating room setting in which it is desired to determine an in vivo blood property, e.g., a hematocrit level (whether relative or absolute) of a patient. The determination can be noninvasive and allows for continuous monitoring without drawing blood. Subcutaneous veins can be illuminated and imaged to aid alignment. The in vivo property can be determined based on diffusely reflected light resulting from near infrared illumination.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Figure 1:
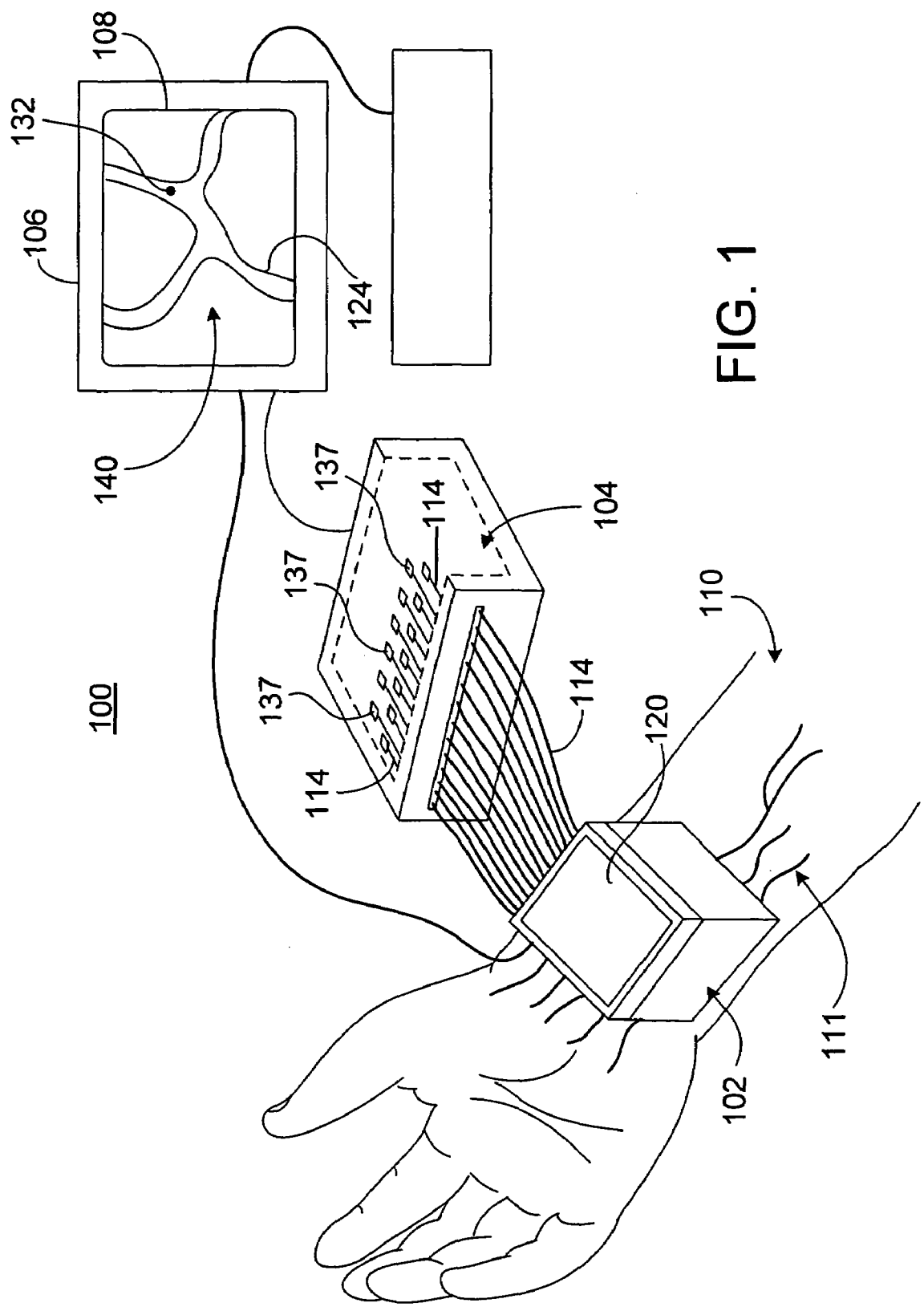
FIG. 1 is a schematic of a system for determining an in vivo property of a tissue or blood of a human or animal. The system is shown ready for an exemplary determination with a sensor module positioned to illuminate a wrist of a human subject with light and to detect light resulting from the illumination.
Figure 2:
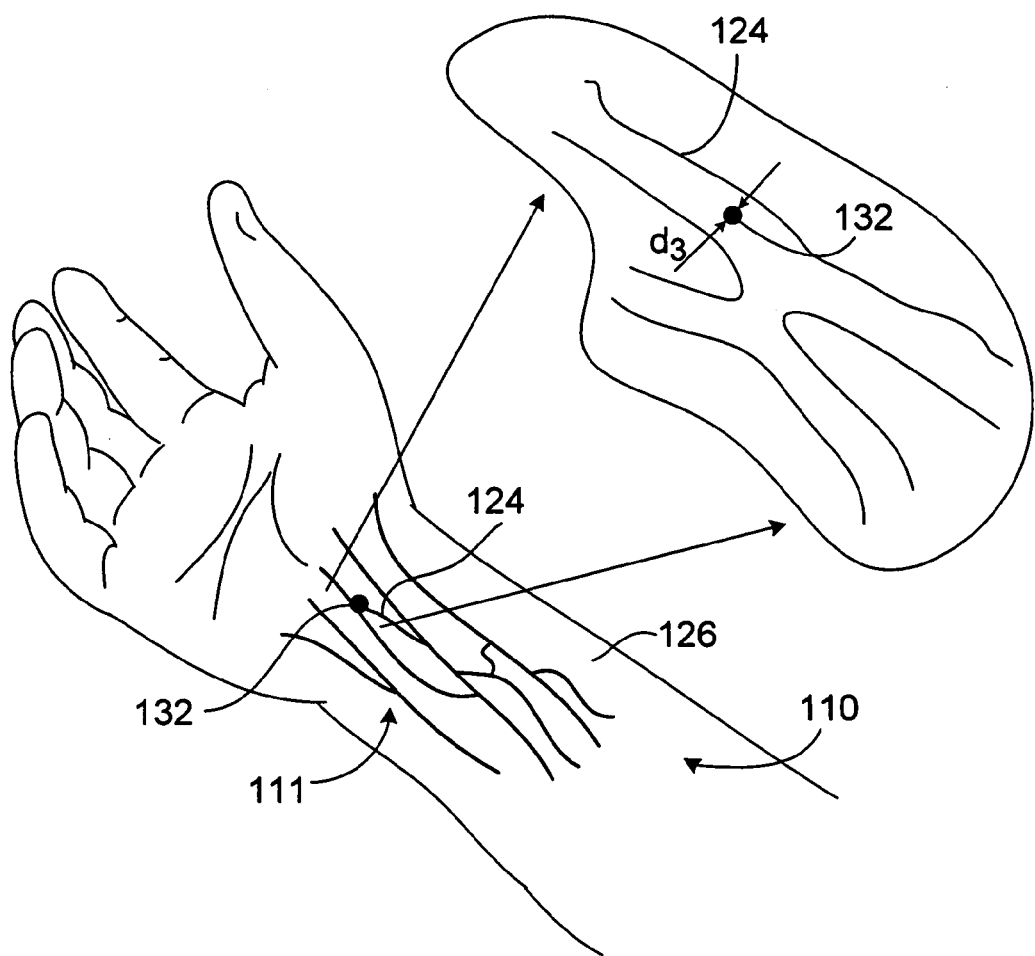
FIG. 2 is a schematic representation of an exemplary spatial relationship between a light beam projected by the sensor module of the system of FIG. 1 and a blood vessel of the wrist.
Figure 3:
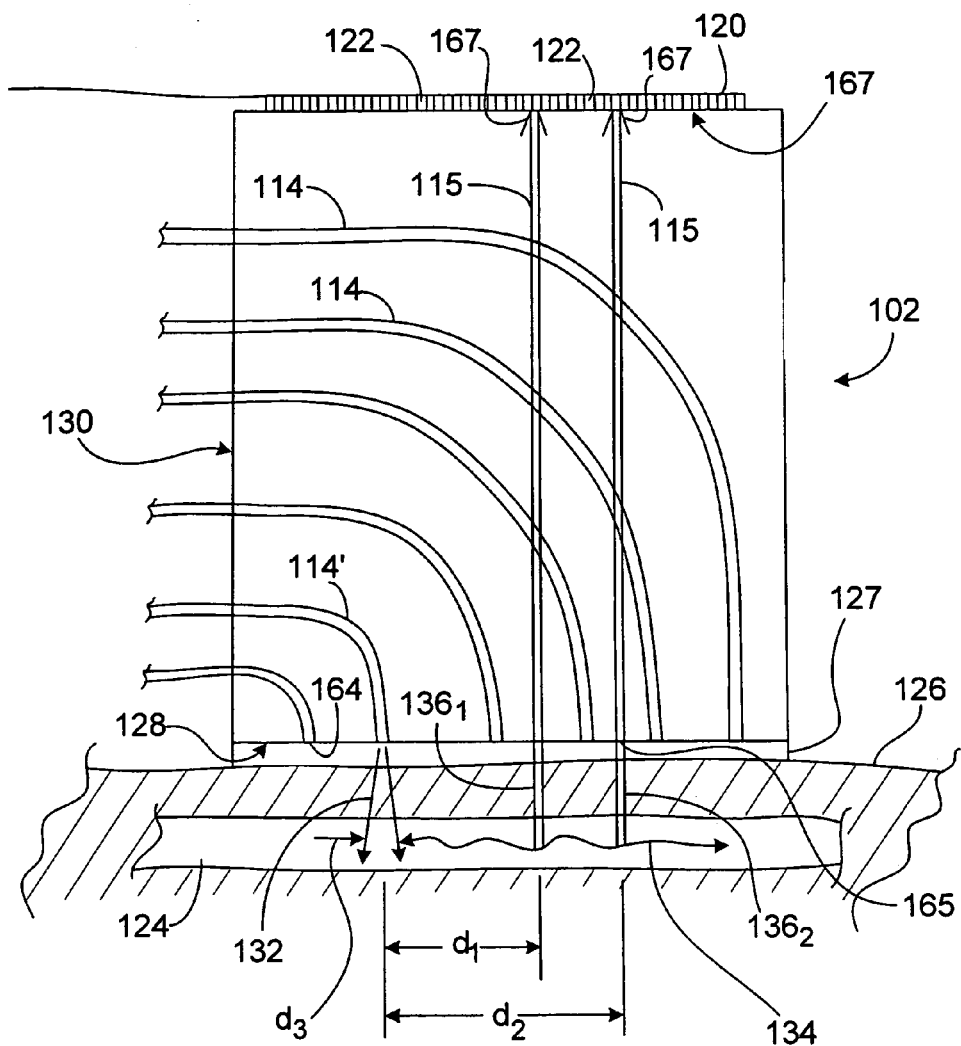
FIG. 3 is a cross-sectional side view of the sensor module of the system of FIG. 1 positioned as shown in FIG. 1. The sensor module projects a light beam, which passes through the skin and illuminates a blood vessel of the wrist.

Referring to FIGS. 1–3, a system 100 determines at least one in vivo property of a tissue or blood of a mammal, e.g., a human subject. In some embodiments, the system determines a hemoglobin (Hb) concentration, an Hct value, or combination thereof of blood of the subject. System 100 includes a sensor module 102, a light source 104, a processor 106, and a display 108. In an exemplary use, an operator positions an optical face 128 of the sensor module 102 generally adjacent a human wrist 110, which has a network 111 of subcutaneous blood vessels. Sensor module 102 illuminates the wrist, e.g., with light from source 104, and detects light that is reflected or scattered from subcutaneous tissues including blood vessels of network 111. The display 108 displays an image 140 corresponding to the subcutaneous tissues. In the image 140, blood vessels appear darker than the surrounding tissues because the blood vessels absorb the illuminating light more strongly. Based on the image, the operator can adjust the sensor module to illuminate a blood vessel with a light beam. Alternatively, the processor can automatically determine a relative location of a blood vessel with respect to the sensor module and operate the light source 104 to illuminate the blood vessel with the projected light beam. In any event, the sensor module 102 detects light that has interacted with blood passing through the illuminated vessel. The processor 106 determines the in vivo blood property based on the detected light.

Figure 4A:
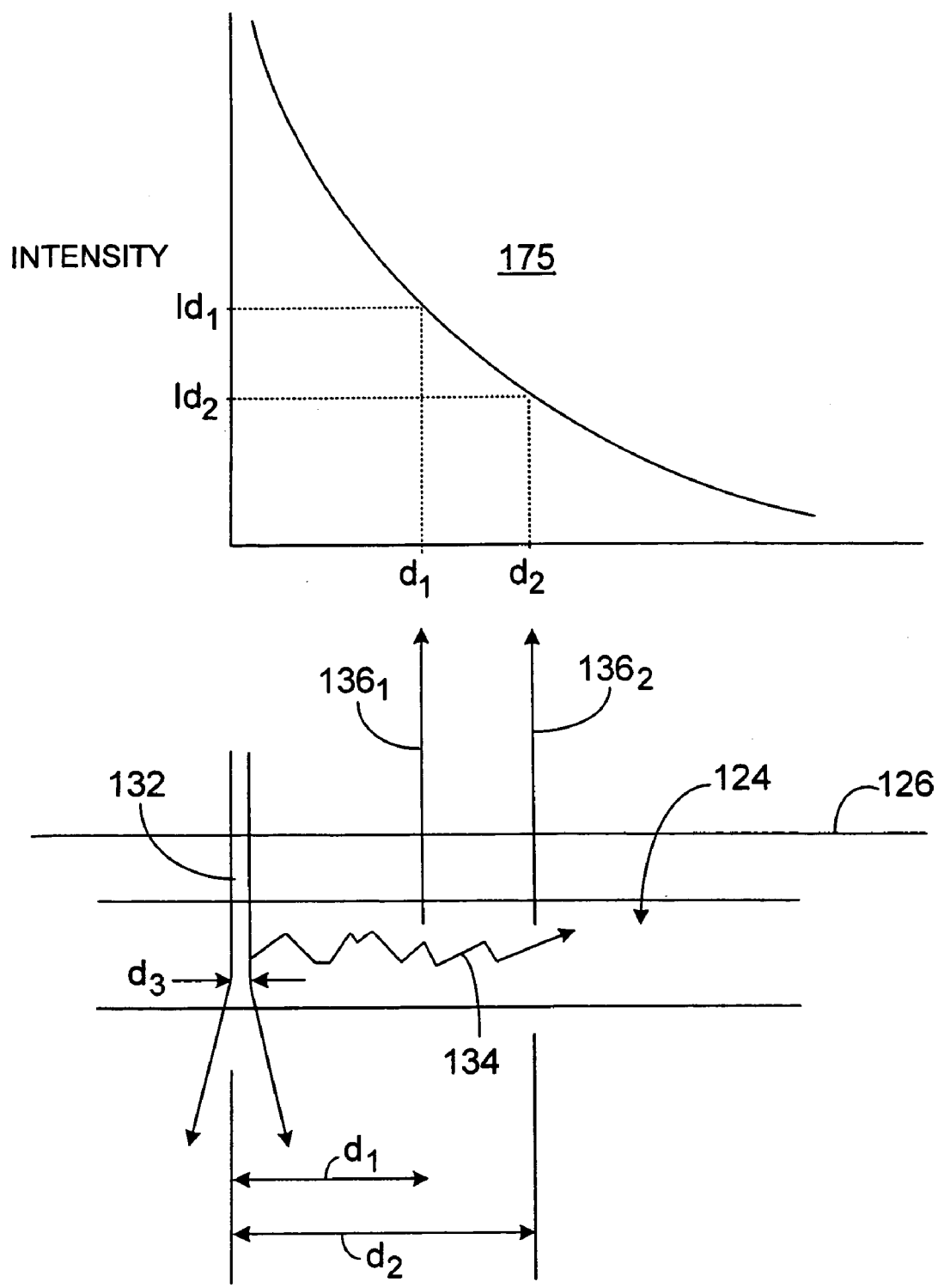
FIG. 4A is a graph that illustrates the change in intensity with distance for light propagating within the blood vessel away from a light beam projected by the sensor module as shown in FIG. 3.

Referring also to FIG. 4A, an exemplary determination of an Hb concentration or Hct value is further described. Light from light source 104 projects as a light beam 132 from the optical face 128. The light beam 132 passes through skin 126 and illuminates at least one subcutaneous blood vessel 124 of the wrist. In general, the light beam 132 intersects at least a portion of the blood vessel. The light beam interacts with components of blood in the vessel, e.g., by absorption, scattering, and/or reflection. As seen schematically in FIGS. 3 and 4A, the interaction causes at least a portion 134 of the light to propagate within the blood vessel 124. At least some of light 134 is then directed back out of the blood vessel and through the skin by scattering, reflection and/or other processes. As examples, light $136_1$ passes out of the blood vessel and exits the skin at a distance $d_1$ from light beam 132 and light $136_2$ passes out of the blood vessel and exits the skin at a greater distance $d_2$ from light beam 132. As will be discussed further below, light $136_1$ and $136_2$ is received by optical face 128 of sensor module 102 and detected by a multidimensional detector, e.g., a CCD 120 having a plurality of pixels 122, which can distinguish between light exiting the skin at different locations with respect to the light beam 132. System 100 can determine an Hb concentration or an Hct value based on the intensities of light exiting the skin at two or more different locations with respect to an illuminating light beam. In embodiments, a difference $\Delta d$ between distances $d_1$ and $d_2$ is greater than a dimension $d_3$ of light beam 132 taken generally along the propagation dimension of light 134. Knowledge of the exact pathlengths traveled by light $136_1$ and $136_2$ within the blood vessel is generally not necessary to determine the in vivo property.

Figure 4B:
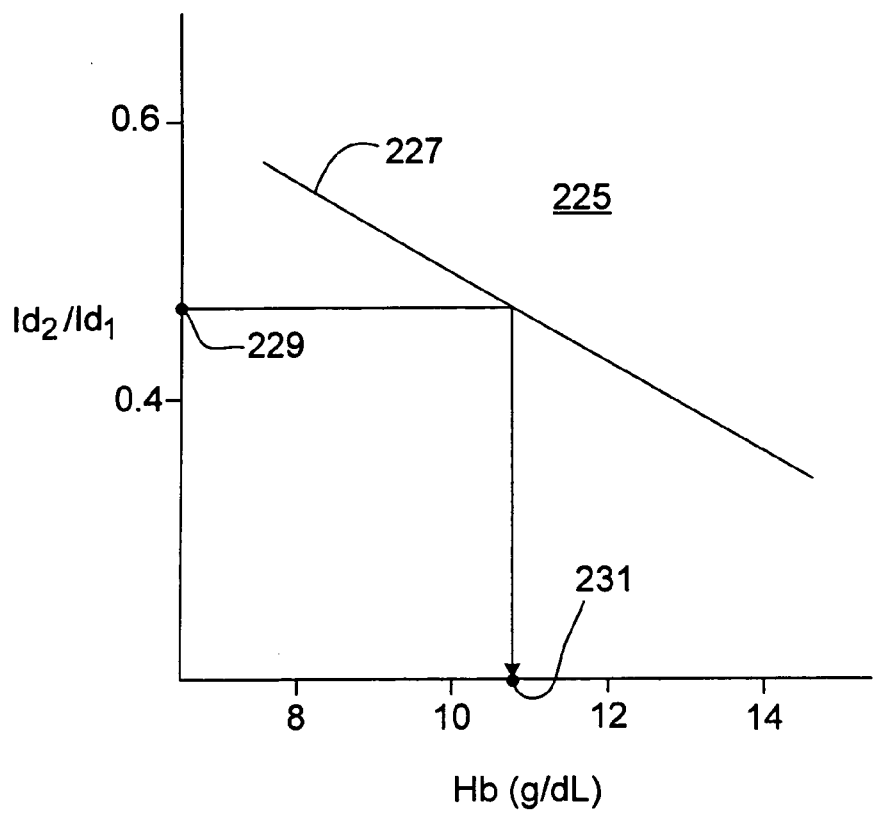
FIG. 4B is a plot showing the change in the ratio of the intensity for light detected at different distances from an illuminating light beam.
Figure 4C:
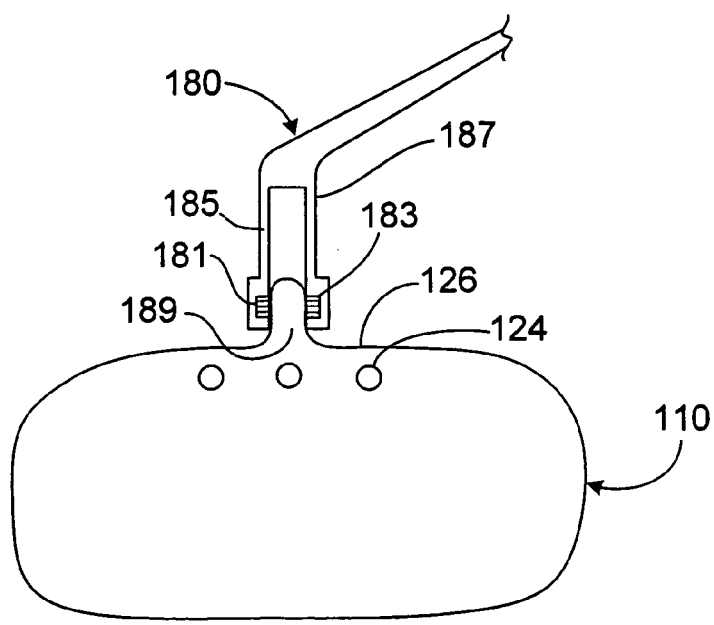
FIG. 4C is a schematic of a probe for determining a contribution from skin and certain subcutaneous tissues to measurements made with the system of FIG. 1.

Intensities $Id_1$, $Id_2$ depend upon the distances traveled within the blood vessel and upon properties of the blood, e.g., the Hb concentration or Hct value. As shown in the intensity-distance graph of FIG. 4A, the farther light travels within the blood vessel, the lower its intensity upon exiting the skin. For example, light $136_1$ has an intensity $Id_1$ and light $136_2$ has a smaller intensity $Id_2$. Referring to FIG. 4B, a line 227 of a plot 225 shows that the ratio of intensities $Id_2/Id_1$ decreases with increasing hemoglobin (Hb) concentration. The Hct value is determined as the percentage of total blood volume occupied by red blood cells, which is proportional to the Hb concentration.

In some embodiments, the relationship between intensities $Id_1$, $Id_2$ and the Hb concentration or Hct is predicted theoretically, as with a photon diffusion model. The theoretical model can include variables such as the wavelength of illuminating light, the scattering and absorption cross-sections of red blood cells and other blood components at the illuminating light wavelength, and the difference between distances $d_1$ and $d_2$. In FIG. 4B, line 227 is representative of predictions determined with such a model. Measured intensities $Id_1$, $Id_2$ or a function of these intensities are compared with the theoretical predictions to determine the Hb concentration and/or Hct. For example, a measured ratio 229 corresponds with an Hct value 231. Theoretical models and parameters useful for such models are discussed in, e.g., Reynolds, L. O., Optical Diffuse Reflectance and Transmittance From An Anisotropically Scattering Finite Blood Medium, Ph.D. Thesis, Dept. Electrical Eng., Univ. of Wash., 1975; Reynolds, L. O. et al. Diffuse Reflectance From A Finite Blood Medium: Applications To The Modeling Of Fiber Optic Catheters, Applied Optics, 15(9), 2059–2067, 1967; and Bohren, C. F. et al., Absorption and Scattering of Light by Small Particles, New York, Wiley & Sons, 477–482, 1983, each of which documents is incorporated herein by reference.

The intensities $Id_1$, $Id_2$ detected by system 100 may also depend on scattering or absorption of the light by the skin and non-blood subcutaneous tissue. System 100 can be configured to measure or determine the extent of such interaction. In various embodiments, system 100 includes a probe 180 having first and second probe arms 185, 187 respectively having a light source 181 and a detector 183. In the embodiment shown, probe 180 is configured to detect light transmitted by a flap 189 of skin 126 of the subject's wrist 110. In alternative embodiments, light source 181 and detector 183 are located in the same probe arm. The light source and detector may be spaced apart from one another within the probe arm. Hence, the arrangement can provide detector signals indicative of propagation within the skin and subcutaneous tissues in the absence of large blood vessels, e.g., blood vessels having a diameter greater than about 1000 µm, 500 µm, 250 µm, or 125 µm. The light source need not emit light at the same wavelength as light used to determine the in vivo blood property.

The probe arm opposite the light source may include a medium that prevents light that reaches the opposite probe arm from reentering the skin and being detected. In various embodiments, the opposite probe arm includes a medium having optical properties indicative of a response of blood having a particular Hct or Hb. In any event, probe 180 generates a detector signal from the detected light. Based on the detector signal, processor 106 can determine a contribution of the skin 126 and/or non-blood subcutaneous tissue to measurements made with sensor module 102.

In some embodiments, sensor module 102 itself measures light intensities indicative of contributions by skin and non-blood subcutaneous tissue. For example, sensor module 102 may illuminate a portion of the skin without directly illuminating a large blood vessel. Such illumination can be achieved by, e.g., illuminating a location of the skin not directly overlying a blood vessel with an illumination angle about normal to the skin or by illuminating the skin at an angle of less than 90° so that the illuminating beam avoids a subcutaneous vessel. The light may have a different wavelength than light used to illuminate a blood vessel, e.g., to obtain intensities $Id_2$ and $Id_1$. For example, the light may have a wavelength that is relatively more highly scattered or absorbed by the skin and subcutaneous tissue than the light used to obtain intensities $Id_2$ and $Id_1$. A sensor module can include a spatial filter to enhance the depth discrimination of the detected light. For example, light can be detected using confocal detection. In any event, the module 102 detects light resulting from the illumination at one or more locations with respect to the illuminating beam. Because the detected light has generally not propagated a significant distance within a large blood vessel, the light can be used to determine the contribution of the skin and non-blood subcutaneous tissue.

The determination of a blood property by system 100 can include correcting detected light intensities, e.g., to subtract, contributions from the skin and non-blood subcutaneous tissue. For example, the contribution of skin and non-blood subcutaneous tissue can be subtracted from each of intensities $Id_1$, $Id_2$ before comparing these values or a function including these values to theoretical predictions. Other corrections can also be applied. For example, one or both of intensities $Id_1$, $Id_2$ can be normalized with respect to an intensity of detected light that has not propagated within a large blood vessel and/or an intensity of detected light that is more highly scattered or absorbed by the skin. System 100 is not limited to determinations of in vivo blood properties based on the ratio of two or more detected light intensities, whether corrected for contributions from skin and non-blood subcutaneous tissue or not.

System 100 can assist an operator in positioning the light beam 132 to illuminate the blood vessel. In some embodiments, sensor module 102 obtains optical data, whether digital or analog, from the subcutaneous network 111 of blood vessels. Display 108 presents the optical data as an image 140, which indicates relative positions of the light beam 132 and one or more blood vessels of the network 111 of blood vessels (FIG. 1). Based on the image, an operator can determine, e.g., whether the light beam illuminates (or will illuminate) or is offset (or will be offset) from a given blood vessel. The operator adjusts the light beam to illuminate the blood vessel by, e.g., changing the relative position of the sensor module 102 and wrist 110. Once a selected spatial relationship between the light beam and a blood vessel has been achieved, the system determines the in vivo blood property based on detected light.

In some embodiments, system 100 automatically determines a location of a subcutaneous blood vessel based on optical data obtained by the sensor module. Processor 106 processes the optical data of the wrist to locate regions that correspond to one or more blood vessels of network 11. Unless otherwise specified, such determined locations may be relative, e.g., relative to some portion of sensor module 102 or to the light beam 132.

System 100 performs one or more different actions upon determining the location of the one or more blood vessels. In some embodiments, system 100 determines whether the sensor module is positioned to illuminate a subcutaneous blood vessel with a light beam. If the sensor module is not so positioned, system 100 can alert the operator, e.g., with a visual or audio signal. The operator then adjusts the sensor module with respect to the wrist. Alternatively, or in combination, the operator uses the system to change the location of the wrist to be illuminated by the light beam. In any event, the system can alert the operator with a signal when the light beam is positioned to illuminate a blood vessel. Once a selected spatial relationship between the light beam and blood vessel is achieved, the system illuminates the blood vessel with light and determines the in vivo blood property.

In some embodiments, system 100 selectively illuminates a blood vessel based on an automatically determined location of the blood vessel. The selective illumination may be automatic. For example, based on optical data obtained by sensor module 102, the processor 106 selects a location of the wrist 110 to be illuminated with a light beam. In various embodiments, the selected location is the skin 126 overlying a subcutaneous blood vessel. In any event, the processor 106 controls the system, e.g., light source 104 and/or sensor module 102, to selectively illuminate the location with a light beam. The processor determines the in vivo blood property based on detected light resulting from the selective illumination. For example, the selective illumination can allow the detection of light that has propagated each of at least two different distances from the illuminated portion of the blood vessel.

In some embodiments, the system can determine the location of a blood vessel and the in vivo blood property from the same optical data. For example, the sensor module 102 may illuminate each of a plurality of discrete locations of the wrist and detect light resulting from the illumination of each discrete location. In general, the detected light resulting from the illumination of each discrete location can be distinguished, whether spatially or temporally, from the detected light resulting from the illumination of other locations. The processor determines the location of a subcutaneous blood vessel based on the detected light. Based on the relative positions of the illuminated locations with respect to the blood vessel, the processor determines whether the illumination of a particular one (or more) of the discrete locations resulted in the illumination of the blood vessel. If so, the system can determine the blood property based on light that was detected upon the illumination of the particular discrete location. Alternatively, or in combination, the system can illuminate the particular location one or more additional times and determine the in vivo property based on light detected upon the additional illuminations.

In some embodiments, system 100 determines a relative Hb concentration and/or Hct value. For example, system 100 can be used to monitor a subject's Hb or Hct at different points in time, as during a surgical procedure. As lost blood is replaced with plasma or other blood substitute lacking red blood cells, the subject's Hb or Hct values decrease. System 100 can monitor such decrease (and any increase upon replenishing the red blood cell population) without necessarily determining the absolute Hb or Hct value. A medical practitioner can introduce fluids and/or red blood cells to the subject based on the relative Hb or Hct values.

Referring back to FIG. 1, components of system 100 are now discussed in further detail. Light source 104 provides light having a wavelength suitable for determining a location of a blood vessel and/or for determining an in vivo property of blood or tissue. Exemplary light sources include lamps, e.g., incandescent sources, and solid-state sources, e.g., light emitting diodes or diode lasers. The light source may emit light in the visible (e.g., with a wavelength of from about 630 to about 670 nm), near infrared (e.g., with a wavelength of from about 670 to about 1000 nm), or infrared (e.g., with a wavelength of from about 1000 nm and about 1500 nm). In some embodiments, the light source emits light having a narrow bandwidth, e.g., less than about 25 nm at full width half maximum (FWHM). The emitted light may be centered about a selected wavelength, e.g., about 802 nm, about 820 nm, or about 880 nm. In various embodiments, the narrow band light has a wavelength centered about an isobestic point of a tissue or blood component. For example, the light may have a wavelength that corresponds to the isobestic point of oxygenated and de-oxygenated hemoglobin forms.

Figure 5:
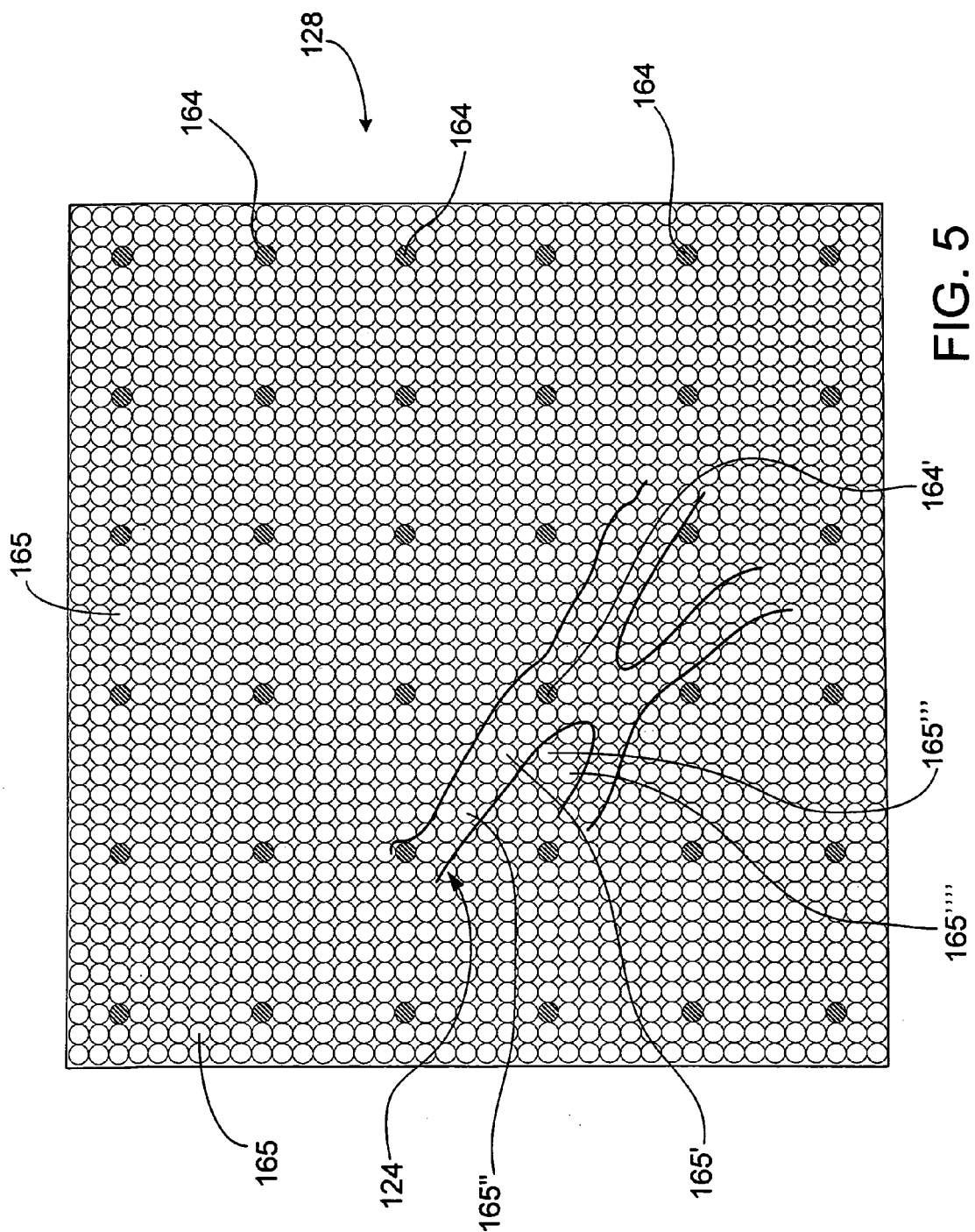
FIG. 5 is a schematic of an optical face of the sensor module of the system of FIG. 1. The optical face includes a first set of terminal optical fiber ends arranged to project a pattern of light beams onto the skin of the wrist and a set of optical fiber entrances arranged to transmit light received by the optical face to a detector.
Figure 6:
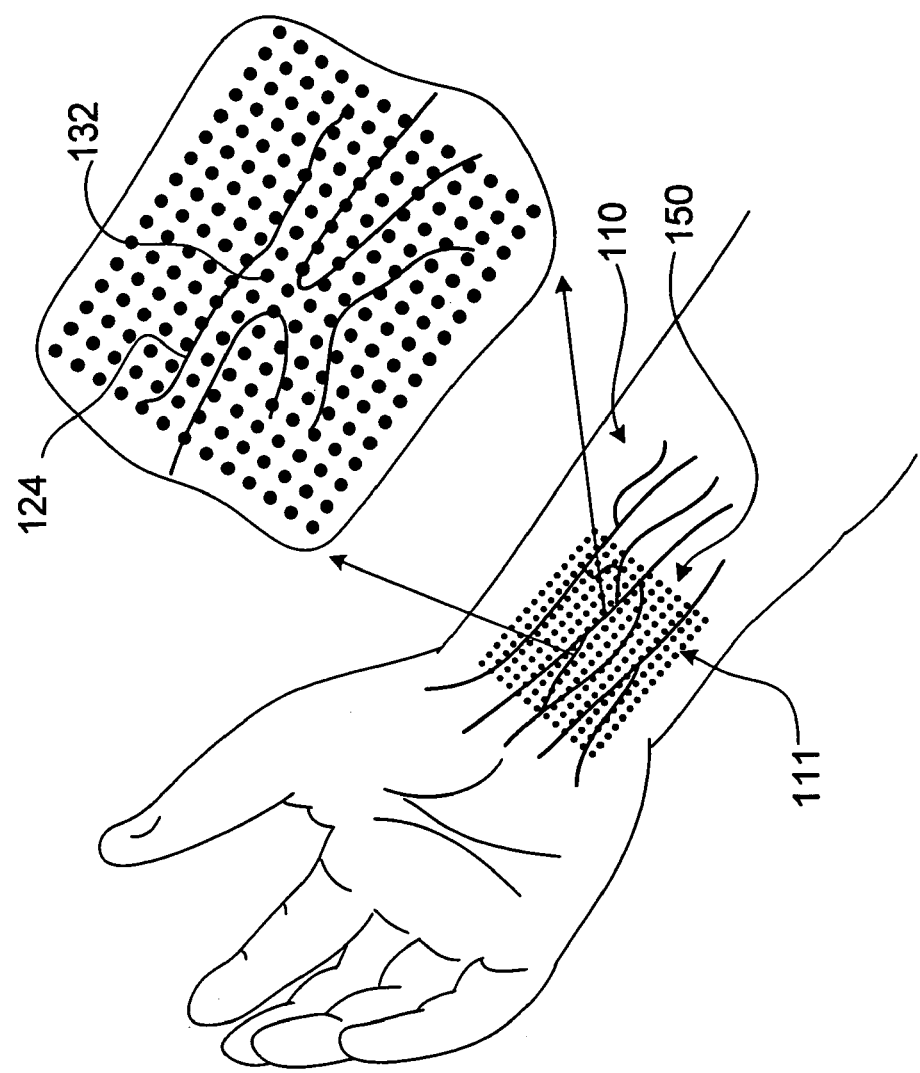
FIG. 6 is a representation of a pattern of light beams projected onto the wrist by the sensor module of the system positioned as shown in FIG. 1. The inset illustrates a spatial relationship between light beams of the projected pattern and several blood vessels.

Referring also to FIGS. 5 and 6, sensor module 102 projects light from the light source as a pattern 150 of discrete light beams onto the subject. Light is transmitted from the light source to the optical face of the sensor module by a plurality of optical fibers 114, each of which terminates at a respective terminal end 164. The terminal ends 164 are arranged in a pattern of rows and columns about the optical face 128. The pattern 150 of projected light beams corresponds to the pattern of terminal ends 164.

Although FIGS. 3 and 5 illustrate a 6×6 pattern of terminal ends 164, sensor module 102 can include more or fewer terminal ends 164. Embodiments of sensor module 102 include a sufficient number of terminal ends 164 such that when sensor module 102 is positioned adjacent an adult human wrist at least one of the ends projects a light beam to illuminate a blood vessel having a diameter of at least about 300 µm or more, e.g., about 500 µm or more. Embodiments of sensor module 102 may include at least 20, at least 50, at least 75, or at least 100 terminal ends 164 at optical face 128. The terminal ends of the optical face 128 may be arranged over an area of about 5, 8, 15 cm$^2$, or 20 cm$^2$. The pattern of terminal ends may include a varying density of ends 164. In various embodiments, the density variation corresponds to the distribution of vessels within network 111, with the greatest density of terminal ends corresponding generally with the pattern of blood vessels of a subcutaneous region, e.g., of the human wrist.

In some embodiments, the light beam projected by each optical fiber 114 has a diameter (not accounting for the optical effects of propagation through tissue) of less than a blood vessel to be illuminated. For example, each optical fiber 114 may project a beam having a diameter (FWHM) of about 1500 µm or less, about 1000 µm or less, about 500 µm or less, e.g., about 250 µm or less within about 4 mm from the terminal fiber end 164. In the embodiment shown, a coupling element 127 is disposed between the optical face 128 and skin 126. Coupling element 127 can include, e.g., a gel, a viscous liquid, or polymer sheet to reduce scattering that might occur at the air-skin interface and air-optical face interface.

The light beam projected by each fiber 114 need not be circular. For example, the light beam may be square or elongated in at least one dimension. In such embodiments, the light beam may have a minor dimension having a width (FWHM) corresponding to the aforementioned light beam diameters.

System 100 can be configured so that terminal ends 164 project light beams individually, simultaneously, sequentially, or in subsets of less than all the terminal ends. For example, in the embodiment shown, each fiber 114 is coupled to a respective light emitting diode 137. Processor 106 operates some or all of the diodes independently of the others to project any combination of light beams from terminal ends 164 of optical face 128.

In alternative embodiments, light source 104 includes only one or a few light sources, each coupled to more than one fiber 114. The terminal ends 164 of the fibers 114 coupled to any one light source can be spaced apart at optical face 128 so that detected light resulting from the illumination by each optical fiber 114 can be distinguished from detected light resulting from illumination by other optical fibers 114. Embodiments can include micro-actuated mirrors, shutters, liquid crystal filters, or the like to selectively couple light to one or more selected fibers 114 associated with a single light source.

As seen in FIG. 3, optical fibers 114 enter sensor module 102 via a side 130 and traverse an arcuate path to reach optical face 128. The optical fibers forming terminal ends 164 along a given row are aligned vertically to limit the area obscured by the fibers. Fibers 114 need not extend all the way to optical face 128.

Figure 7:
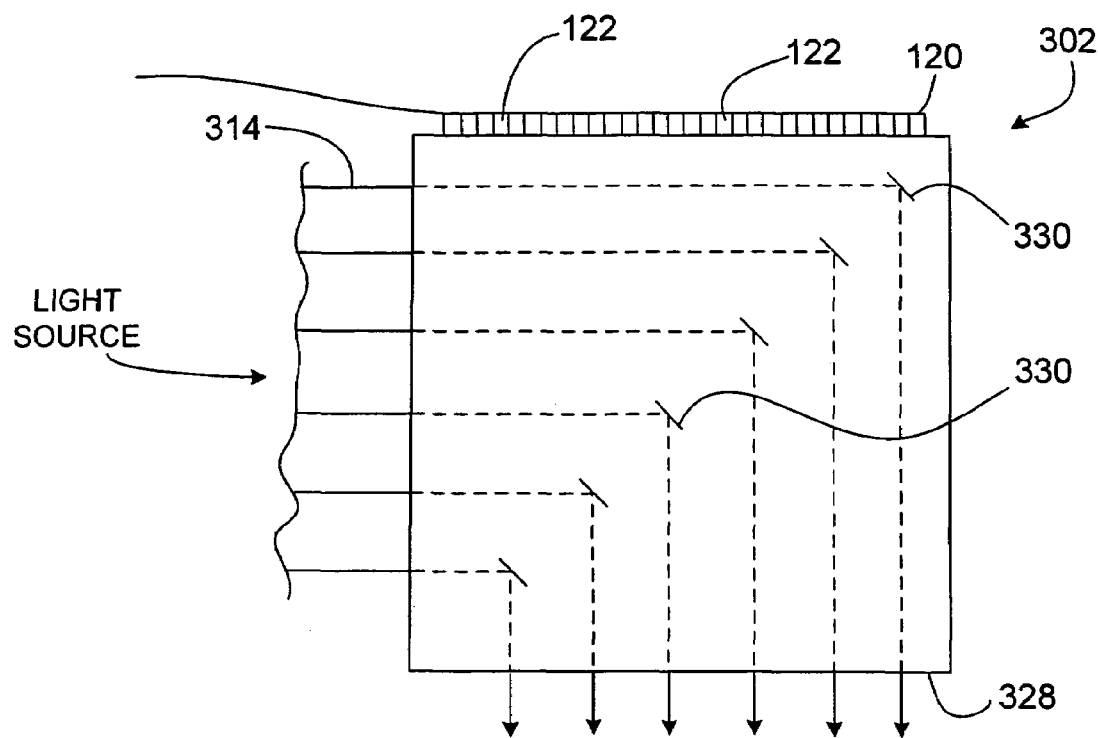
FIG. 7 is a side view of another sensor module.

Referring to FIG. 7, a sensor module 302 includes a plurality of directional elements 314, e.g., micro-mirrors or prisms, configured to direct light from a light source from a side 330 of the sensor module toward an optical face 328. The directional elements 314 along a given row can be arranged in staircase fashion to direct light introduced along different paths through the sensor module toward optical face 328. A sensor module can include fibers to guide light to an interior of the sensor module and directional elements to direct the light to an optical face of the module. The fibers or light guides that guide light from a periphery of the sensor module to an interior of the sensor module can be spaced apart from the optical face of the module as in module 102 or can extend along the optical face itself. In some embodiments, light sources, e.g., LED's, are positioned to project light from the optical face without a fiber or directional element. For example, the light sources may be disposed within a sensor module.

Returning to FIGS. 1 and 3, properties of light, e.g., its intensity, directed back through the skin at different locations with respect to an illuminating light beam depend at least in part on the distribution of subcutaneous blood vessels and in vivo blood properties. In general, sensor module 102 can preserve spatial properties, e.g., the relative intensity distribution, of light that has exited the skin and been received by optical face 128. Pixels 122 of multidimensional detector 120 can detect and distinguish, e.g., spatially, light received by different locations of optical face 128. Hence, detector 120 can provide a detector signal based on which the processor can, e.g., prepare an image of subcutaneous features, determine a location of a blood vessel, or determine an in vivo blood property. A detector signal indicative of an intensity or other property of detected light is referred to herein as optical data.

In various embodiments, processor 106 receives optical data from detector 120. Processor 106 distinguishes blood vessels from the surrounding subcutaneous media based on properties of the detected light, e.g., the intensity and varying contrast of the detected light. For example, processor 106 may subject the optical data to segmentation, e.g., by threshold techniques, edge-based methods, region-based techniques, or connectivity-preserving relaxation techniques. Processor 106 may determine boundaries between vessels and surrounding media, such as by use of continuous edges and/or allowable bifurcation patterns of network 111. The optical data may be subjected to edge and/or contrast enhancement to better differentiate vessels from surrounding media. Once one or more vessels have been located, e.g., with respect to a portion of sensor module 102, processor 106 selects an appropriate fiber 114 with which to illuminate the vessel.

In the embodiment shown, sensor module 102 includes a plurality of light guiding elements 115 (only two of which are shown in FIG. 3) to guide light received by different locations of optical face 128 to different pixels 122 of detector 120. Each light guiding element 115 has an entrance aperture 165 at the optical face 128 and a terminal end 167 located at an opposite face 169 of the sensor module. Each of a plurality of terminal ends 167 (e.g., all of the terminal ends) are optically coupled to at least one pixel 122 of detector 120. Each of a plurality of pixels 122 (e.g., all of the pixels) are optically coupled to at least one terminal end 167. Hence, sensor module 102 can obtain an image of subcutaneous features without a lens or other optic with focusing power. In various embodiments, light guiding elements 115 include a plurality of waveguides, a plurality of optical fibers, one or more optics with focusing power, e.g., one or more lenses or mirrors, or combination thereof. Sensor module can include a beam splitting optic to direct light toward the subject yet allow a portion of light exiting the skin to pass through the beam splitting optic to detector 120.

Returning to FIG. 5, an exemplary spatial relationship between a given terminal end 164', blood vessel 124, and entrances 165', 165" to two different optical fibers 115 is illustrated. Upon determination of the location of blood vessel 164', system 100 illuminates the blood vessel 124 via a light beam projected from the terminal end 164' of a fiber 114. Light resulting from the illumination and exiting the skin can be received by any of the fiber entrances 165 and detected by detector 120. Light received by fiber entrances 165' and 165", however, has passed respective, different distances within blood vessel 124. An in vivo blood property can be determined based upon the light intensity detected by pixels 122 coupled to light guiding elements 115 extending from entrances 165' and 165". On the other hand, light received by entrances 165''' and 165''' will have passed approximately the same distance within vessel 124 before passing out of the blood vessel and into the surrounding subcutaneous media, e.g., tissue. Based on the spatial relationship between the vessel 124 and the projected light beam, processor 106 can select the light guiding elements 115 that will be used to collect light for determining the in vivo blood property. For example, processor 106 may select fibers that intersect the blood vessel at longitudinally or axially aligned locations with respect to the illuminating light beam.

In various embodiments, sensor module 102 includes a sufficient number of light guiding elements 115 and pixels 122 to provide optical data with a resolution sufficient to allow an operator to adjust the position of a light beam with respect to a subcutaneous blood vessel and/or to allow processor 106 to automatically determine the location of a blood vessel based on the optical data. Sensor module 102 can include at least 1, 50, 250, 1000, 2500, or more light guiding elements 115. In various embodiments, the centers of adjacent fiber entrances 165 are spaced apart along at least one dimension by less than about 250, 125, 75, 25 µm, or less.

As shown in FIG. 1, optical data from detector 120 can be displayed as image 140 including one or more blood vessels of network 111. In some embodiments, the image 140 may not include an image of some or all light beams projected from terminal ends 164 because the fibers 114 extending within the sensor module can block light from reaching detector 120. Nonetheless, an operator or processor 106 can determine whether a given terminal end 164 is aligned with a blood vessel based on light received by fibers 115 in the vicinity of the given fiber 114. Such a condition exemplifies that optical data output by the sensor module need not expressly include a light beam to be indicative of a spatial relationship between the light beam and a blood vessel.

Figure 8:
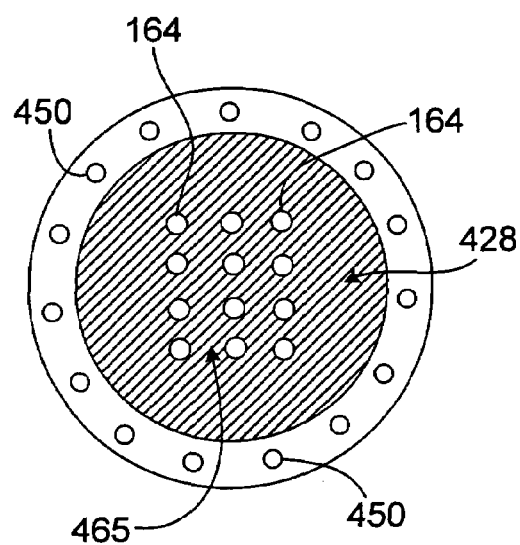
FIG. 8 is schematic diagram of an optical face of a sensor module. A plurality of light sources surround the optical face.

Referring to FIG. 8, a sensor module 402 includes an optical face 128 having a plurality of terminal fiber ends 164 for projecting light from the optical face. A region 465 of the optical face is configured to receive light and transmit the light to a detector. A plurality of light emitting elements 450, e.g., terminal optical fiber ends or light emitting diodes, surround the optical face 428. Light emitting elements 450 illuminate generally the subcutaneous area beneath optical face 428. Processor 106 can determine, e.g., a location of a blood vessel based on light detected upon illumination with elements 450. Processor 106 can then select a terminal end 164 to project a light beam into the blood vessel.

Figure 9:
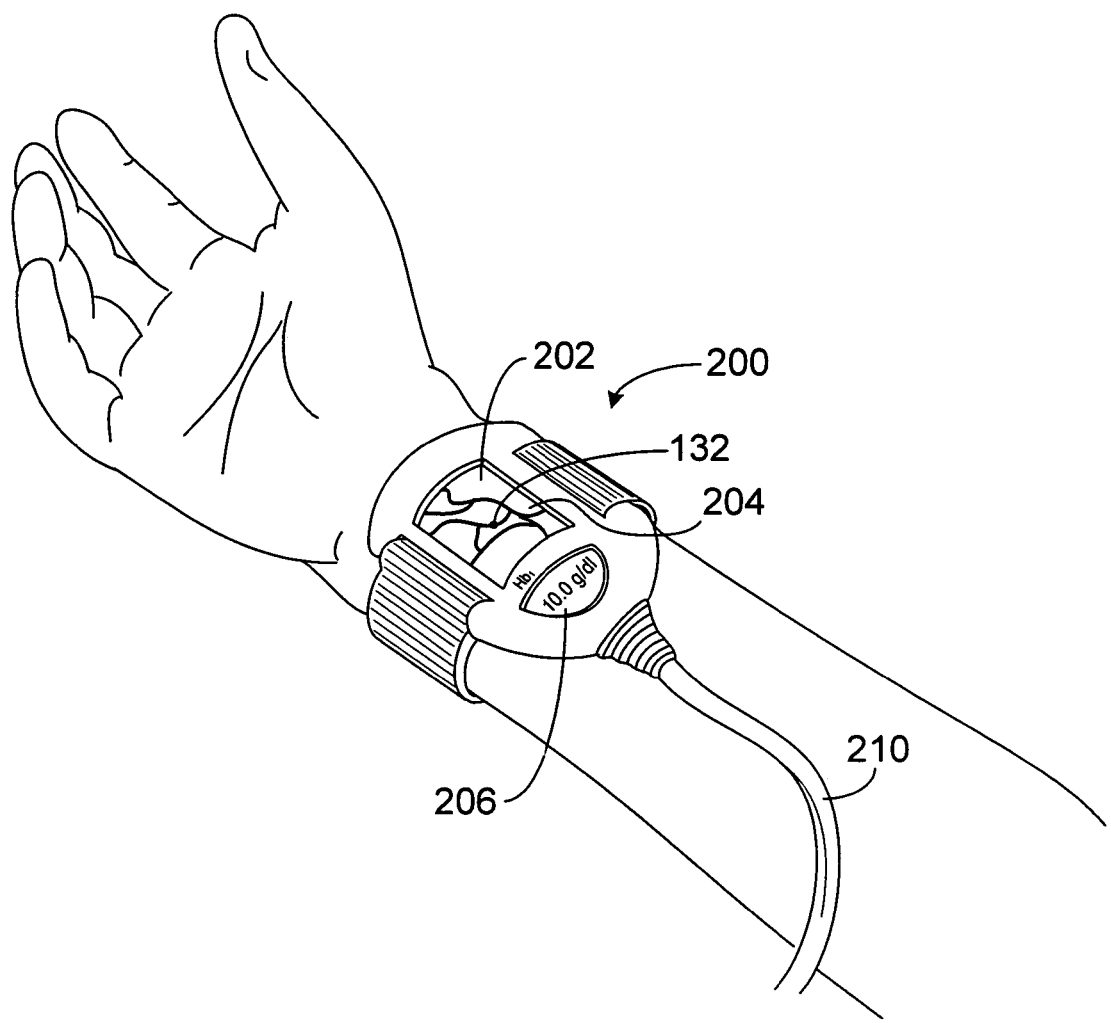
FIG. 9 is a representation of an integrated system for determining an in vivo property of a tissue of a human or animal.

Referring to FIG. 9, an integrated system 200 determines an in vivo property of tissue or blood of a subject. System 200 includes a light source for illuminating skin and subcutaneous tissue of the subject. A multidimensional detector, e.g., a CCD, detects light resulting from the illumination and converts the detected light to optical data. A display, e.g., a liquid crystal display 202, displays the optical data as an image 204 including at least one subcutaneous blood vessel. The image can also include at least one light beam or a marker indicative of a location of the subject to be illuminated by a light beam. Hence, an operator can determine from the display whether the light beam overlaps a blood vessel. Alternatively, or in addition, the processor of the system 200 can automatically determine the location of the blood vessel and selectively illuminate the blood vessel with a light beam.

System 200 also includes an output, e.g., an output display 206 for output of the tissue or blood property, e.g., an Hct value. System 200 can be directly linked via a connector 210 or wirelessly linked to a power supply or processing module for monitoring the tissue or blood property along with other parameters. Connector 210 can include optical fibers for carrying light to or from the system 200. Hence, either or both the light source and detector can be positioned remote from the portion shown.

Once system 200 has been positioned to illuminate a blood vessel, the system can continuously or intermittently determine the tissue or blood property during, e.g., a surgical intervention or diagnostic procedure. An operator can verify at any time that the light beam is properly positioned to illuminate the blood vessel.

Figure 10:
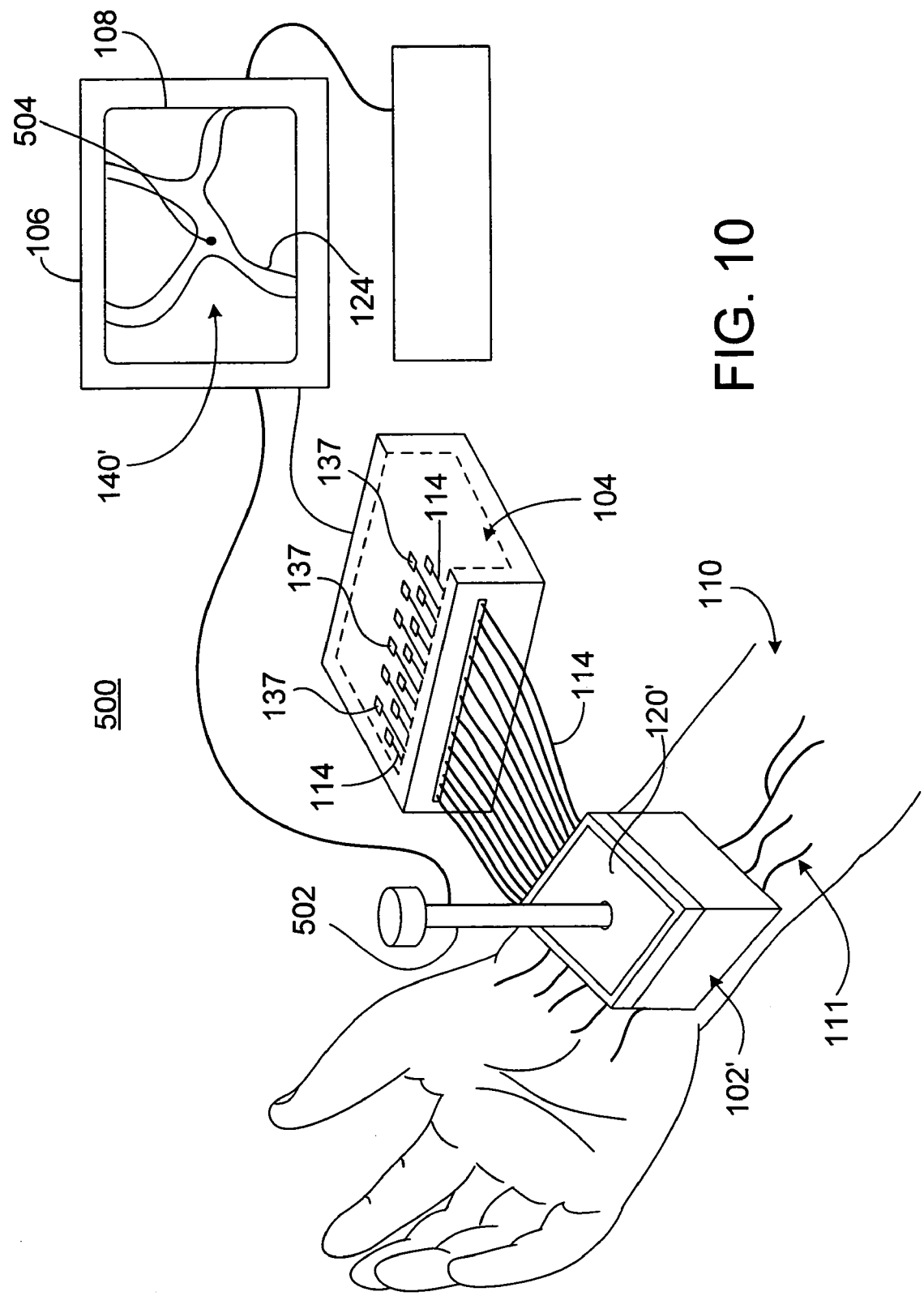
FIG. 10 is a representation of a system for performing an injection and/or marking an injection site.

Referring to FIG. 10, a system includes a modified sensor module 102' having an injection module 502 for performing an injection and/or marking the skin for later manipulation. When configured to perform an injection, module 502 automatically introduces or allows the manual introduction of a material, e.g., blood, saline solution, glucose solution, or medicine, for example, subcutaneously or intravenously, such as by injection via a target site into blood vessel 124. In marking mode, the module 502 may mark the skin, e.g., via ink, at the target site. System 500 can display an image 140' indicative of a spatial relationship between an image of the target site 504 or location that will receive an injected material and one or more subcutaneous features, such as blood vessel 124. For example, the image 140' can indicate whether the injection will be received within a blood vessel or offset from the blood vessel.

In some embodiments, an operator positions sensor module 102' in an operative position with respect to a subject, e.g., with respect to skin of the subject, e.g., adjacent the wrist 110, contacting the skin of the wrist, or spaced apart from the wrist by coupling element 127. The operator manipulates the sensor module while observing the position of target site 504 and subcutaneous features. When a desired spatial relationship is achieved, the operator can manually or automatically inject a material via module 502. The module can include a needle or other injection device. System 500 can be configured to signal the operator when site 504 has a desired spatial relationship with a blood vessel or other subcutaneous feature. Rather than or in addition to injecting a material, the module may simply mark site 504 for later injection or manipulation. Although module 502 is shown oriented normal to the skin, other orientations, e.g., sub-ninety degree angles, with respect to the skin can be used.

Any of the methods discussed herein can be implemented in hardware or software, or a combination of both. The methods can be implemented in computer programs using standard programming techniques following the methods and figures described herein. Program code can be applied to input data, e.g., image data and/or data resulting from detected light, to perform the functions described herein and generate output information. The output information can be applied to one or more output devices such as display 108. Each program may be implemented in a high level procedural or object oriented programming language to communicate with processor 106, e.g., a computer system, handheld processing device, or the like. However, the programs can be implemented in assembly or machine language, if desired. In any case, the language can be a compiled or interpreted language. Moreover, the program can run on or be implemented by dedicated integrated circuits preprogrammed for that purpose.

Each such program can be stored on a storage medium or device (e.g., ROM, compact disk, or magnetic diskette) readable by a general or special purpose programmable processor. The program can also reside in a cache or a main memory during program execution. The analysis methods can also be implemented as a computer-readable or machine-readable storage medium, configured with a computer program, where the storage medium so configured causes a processor to operate in a specific and predefined manner to perform the functions described herein.

OTHER EMBODIMENTS

In the embodiments shown, optical fibers 114 may be fixed with respect to optical face 128. In other embodiments, a sensor module moves, e.g., scans, a light beam with respect to a subject. A multidimensional detector detects light resulting from illumination with the beam. For example, the sensor module may move the beam by scanning the terminus of an optical fiber or by directing the beam with a movable optic, e.g., a positionable mirror.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A system for determining an in vivo blood property, the system comprising:
    an optical device configured to project a light beam onto a tissue of a subject;
    an imaging device configured to generate optical data;
    a device to display an image corresponding to the optical data, wherein the image indicates a spatial relationship between the light beam and a blood vessel within the tissue, and wherein a user can manipulate the optical device and, based on the image, bring the light beam and the blood vessel into a selected spatial relationship wherein the light beam is projected on the blood vessel at a first location on the blood vessel;
    a detector configured to generate a detector signal corresponding to light resulting from illumination of the blood vessel with the light beam having the selected spatial relationship, the detector signal indicating light intensities of light exiting the blood vessel at two or more locations on the blood vessel, the two or more locations being spaced apart from each other and from the first location; and
    a processor configured to determine an in vivo blood property based on the detector signal and the relative positions of the two or more locations on the blood vessel.

2. The system of claim 1, wherein the imaging device is configured to illuminate the tissue with light having a wavelength between about 400 and 1250 nm, and wherein the light illuminating the tissue covers a spatial extent that is substantially greater than a diameter of the blood vessel.

3. The system of claim 1, wherein a first portion of the detector signal corresponds to light that has passed a first distance within the blood vessel and a second portion of the detector signal corresponds to light that has passed a second, different distance within the blood vessel and wherein the processor is configured to determine the in vivo blood property based on the first and second portions of the detector signals.

4. The system of claim 3, wherein the projected light beam, when in the selected spatial relationship with the blood vessel, has a width within the blood vessel that is about the same as or smaller than a difference between the first and second distances.

5. The system of claim 1, wherein the in vivo blood property is a hematocrit, an abundance of hemoglobin, or a combination thereof.

6. A method for determining an in vivo blood property, comprising:
    displaying an image including at least one subcutaneous blood vessel, wherein the image indicates a spatial relationship between a light beam derived from a light source and the blood vessel;
    based on the image, changing the spatial relationship between the light beam and the blood vessel so that the light beam is projected on the blood vessel at a first location on the blood vessel and illuminates the blood vessel;
    detecting light intensities of light exiting the blood vessel at two or more locations on the blood vessel resulting from the illumination of the blood vessel by the light beam, the two or more locations being spaced apart from each other and from the first location;

determining an in vivo blood property based on the detected light intensities and the relative positions of the two or more locations on said blood vessel; and outputting the in vivo blood property.

7. The method of claim 6, wherein changing the spatial relationship comprises manually changing a position of the light beam with respect to the blood vessel.

8. The method of claim 6, wherein determining an in vivo blood property comprises determining a hematocrit, an abundance of hemoglobin, or combination thereof.

9. A system for determining an in vivo blood property, comprising:
a device configured to automatically determine a location of a subcutaneous blood vessel;
a light source configured to illuminate a located blood vessel with light projected on the blood vessel at a first location on the blood vessel;
a detector to detect light intensities of light exiting the blood vessel at two or more locations on the blood vessel resulting from the illumination, the two or more locations being spaced apart from each other and from the first location, and generate a detector signal from the detected light intensities; and
a processor configured to receive the detector signal and determine an in vivo blood property based on the detected light intensities and the relative positions of the two or more locations on said blood vessel.

10. The system of claim 9, wherein the light source comprises a plurality of light guides each configurable to project a light beam onto a respective different portion of a subject's skin.

11. The system of claim 10, wherein the detector is configured to detect light that has passed first and second different distances within an illuminated located blood vessel and wherein the processor is configured to determine the in vivo property based on the light that has passed the first and second different distances.

12. The system of claim 11, wherein the detector comprises a multidimensional detector comprising a plurality of detector elements and at least first and second detector light guides, the first and second detector light guides respectively configured to transmit the light that has passed the first and second different distances to different detector elements.

13. The system of claim 9, wherein the in vivo blood property is a hematocrit, an abundance of hemoglobin, or a combination thereof.

14. A method for determining an in vivo blood property, comprising:
automatically determining a location of a blood vessel of a subject;
illuminating the blood vessel with a light beam projected on the blood vessel at a first location on the blood vessel;
detecting light intensities of light exiting the blood vessel at two or more locations on the blood vessel resulting from illuminating the blood vessel, the two or more locations being spaced apart from each other and from the first location;
determining an in vivo blood property based on the detected light intensities and the relative positions of the two or more locations on said blood vessel; and
outputting the in vivo blood property.

15. The method of claim 14, wherein determining an in vivo blood property comprises determining a hematocrit, an abundance of hemoglobin, or a combination thereof.

16. The method of claim 14, wherein automatically determining comprises:
illuminating skin of the subject with light;
detecting light resulting from the illumination of the skin; and
determining the location of the blood vessel based on the detected light resulting from the illumination of the skin.

17. The method of claim 16, wherein detecting light resulting from the illumination of the skin comprises transmitting light through a plurality of different optical fibers each coupled to at least one detector element of a multidimensional detector.

18. The method of claim 16, wherein detecting light resulting from the illuminating comprises detecting a first portion of light having exited the skin a first distance away from the light beam and a second portion of light having exited the skin a second, different distance away from the light beam, and wherein the in vivo property is determined based on the first and second portions of light.

19. The method of claim 14, wherein illuminating a blood vessel comprises projecting a light beam from a light guide.

20. The method of claim 14, wherein illuminating a blood vessel comprises scanning light over the skin.

21. The method of claim 14, further comprising:
displaying an image indicating a spatial relationship between the blood vessel and a light beam projected onto the skin of the subject, and wherein, based on the image, a user can manually bring the blood vessel and light beam into a selected spatial relationship.

22. A method for determining an in vivo blood property, comprising:
illuminating a portion of a subject with a light from a light source, the illuminated portion of the subject comprising a blood vessel;
detecting light from the illuminated portion of the subject;
determining a location of a blood vessel based on light detected from the illuminated portion of the subject;
illuminating the blood vessel with a light beam projected at a first location on the blood vessel;
detecting first light that has passed a first distance within the blood vessel from the light beam and second light that has passed a second, different distance within the blood vessel from the light beam;
determining an in vivo blood property based on the first and second light and on the first and second distances; and
outputting the in vivo blood property.

23. The method of claim 22, wherein illuminating the portion of the subject and illuminating the blood vessel with a light beam are performed as part of the same step.

24. The method of claim 23, wherein detecting the light from the illuminated portion of the subject and the detecting the first and second light are performed as part of the same step.

25. The method of claim 22, wherein illuminating a portion of a subject with light from a light source comprises scanning the portion of the subject with a light beam.

26. The method of claim 22, wherein determining an in vivo blood property comprises determining a hematocrit value, an abundance of hemoglobin, or a combination thereof.

27. A method for determining an in vivo blood property, comprising the steps of:
identifying a blood vessel of a subject;
illuminating the blood vessel with a light beam projected on a first location on the blood vessel;
detecting light intensities of light exiting the blood vessel at second and third locations on the blood vessel resulting from illuminating the blood vessel, said second and third locations being spaced apart from each other and from the first location;
determining an in vivo blood property based on the detected light intensities and the relative positions of the second and third locations on the blood vessel; and
outputting the in vivo blood property.

* * * * *